(12) United States Patent
Lazakis

(10) Patent No.: US 9,119,480 B1
(45) Date of Patent: Sep. 1, 2015

(54) PRESSURE VARIABLE THERMAL ADAPTIVE MICROCLIMATE SURFACE AND THERMOELECTRIC CELLS FOR MICROCLIMATE SURFACE

(71) Applicant: Theodosius A. Lazakis, Long Grove, IL (US)

(72) Inventor: Theodosius A. Lazakis, Long Grove, IL (US)

(73) Assignee: Alpha Bedding, LLC, Lake Zurich, IL (US)

( * ) Notice: Subject to any disclaimer, the term of this patent is extended or adjusted under 35 U.S.C. 154(b) by 7 days.

(21) Appl. No.: 14/204,245

(22) Filed: Mar. 11, 2014

(51) Int. Cl.
*A61G 7/057* (2006.01)
*A47C 21/04* (2006.01)
*A47G 9/10* (2006.01)

(52) U.S. Cl.
CPC ............ *A47C 21/048* (2013.01); *A47G 9/1036* (2013.01)

(58) Field of Classification Search
CPC ....................................................... A61G 7/057

USPC ........................... 5/421, 423, 710, 713, 652.1
See application file for complete search history.

(56) References Cited

U.S. PATENT DOCUMENTS

| | | | | |
|---|---|---|---|---|
| 7,945,979 B1 * | 5/2011 | Lin | ................................... | 5/726 |
| 2010/0095461 A1 * | 4/2010 | Romano et al. | .................... | 5/710 |
| 2011/0271448 A1 * | 11/2011 | Faridoon | ........................... | 5/423 |
| 2012/0065560 A1 * | 3/2012 | Siegner | ......................... | 601/150 |

* cited by examiner

*Primary Examiner* — Fredrick Conley
(74) *Attorney, Agent, or Firm* — Justin Lampel

(57) ABSTRACT

A pressure variable thermal adaptive microclimate surface is provided. The microclimate surface may be a pad, pillow, mattress or the like. The microclimate surface is especially suitable for providing optimal heating and/or cooling of a person. The heating or cooling is provided through heating or cooling delivery system located in the sculpted polyurethane foam microclimate surface. The microclimate surface has a plurality of independently moving pillars which is optimal in reducing pressure ulcers on the skin of a person caused by the person spending extended periods of time on a typical surface, such as a hospital mattress. The heating or cooling delivery system may be provided through three possible configurations.

19 Claims, 6 Drawing Sheets

PRESSURE VARIABLE THERMAL ADAPTIVE MICROCLIMATE SURFACE AND THERMOELECTRIC CELLS FOR MICROCLIMATE SURFACE

CROSS REFERENCE TO RELATED APPLICATION

The following application is based on and claims the priority benefit of U.S. Provisional Application Ser. Nos. 61/887,818 filed on Oct. 7, 2013, and U.S. Provisional Ser. No. 61/802,779 filed on Mar. 18, 2013; the entire contents of which are incorporated by reference.

BACKGROUND OF THE INVENTION

A pressure variable thermal adaptive microclimate surface is provided. The microclimate surface may be a pad, pillow, mattress or the like. The microclimate surface is especially suitable for providing optimal heating and/or cooling of a person. The device has a pressure variable thermal adaptation function which is embodied in three possible system types. In all three types the pressure thermal adaptivity is produced by the partial compression of the sculpted resilient foam cushioning which (while generally maintaining its skin protecting resilience) reduces the foam's insulation properties (by collapsing the internal air bubbles) and thereby increasing its thermal conductivity proportionally where pressure is applied. Because the location where the greatest pressure is applied is also the area which needs the greatest thermal therapy, the device optimizes the effectiveness of the thermal delivery system. For example, pressure ulcers can form in hospitalized people due to localized persistent pressure and high temperatures under bony prominences such as the sacral (tailbone) region. Healthcare mattresses are made using fluid impervious coated covers to enhance disinfectability. These covers, however also almost completely eliminate the flow of air necessary for our skin's temperature management system, which relies on evaporative cooling from our sweat glands. Without constant airflow these parts of the body become warmer and the un-evaporated perspiration can further reduce skin integrity due to maceration, leading to potential damage such as infections and pressure ulcers. In the current state of the art, liquid or air circulating channels collapse proportionally with applied pressure thereby reducing or eliminating the thermal transfer where it is most needed. With the greater thermal conductivity the invention provides, cooling or heating from the system is efficiently directed to the areas with higher pressure which need the thermal therapy most.

The heating or cooling is provided through a heating or cooling delivery system located in the sculpted polyurethane foam microclimate surface. The microclimate surface has a plurality of independently moving pillars which is optimal in reducing pressure ulcers on the skin of a person caused by the person spending extended periods of time on a typical surface, such as a hospital mattress. The heating or cooling delivery system may be provided through three possible configurations: I) Fluid (cooled or heated) is circulated through a tubing matrix which is placed within the sculpted foam surface using a connected thermoelectric device. The electrically powered device consists of one or more thermoelectric cells, a power supply, a pump, a heat exchanger, a fan, electronic thermostatic controller, and a control panel with a user interface (temperature readout, power on/off, set temp, it may or may not have a timer function); II) Fluid (cooled or warmed) is circulated through a tubing matrix which is placed within the sculpted foam surface using a radiator device. The electrically powered radiator device may be integrated within the mattress or in a separate tubing connected component. The radiator device consists of a pump, a heat exchanger with or without fan, and a user interface; III) The third embodiment incorporates a plurality of small thermoelectric cells which are connected by wiring and inserted into chambers cut into the sculpted foam. These thermoelectric cells are placed so that the thermal therapy side (cooling in this instance) come in closer contact to the patient's body presenting the greatest pressure to the surface. A circulating system of fluid (gas or liquid) is used to draw heat away from the warm side of the thermoelectric cells. This system incorporates a heat exchanger, fluid pump or blower, a controller and a user interface. All three systems may also incorporate one or more separate sensors which can be placed to detect the temperature in localized areas to optimize the setting.

Pressure ulcers, also known as decubitus ulcers or bedsores, are lesions caused by unrelieved pressure on soft tissues overlying a bony prominence which reduces or completely obstructs the blood flow to the superficial tissues. According to the Agency for Healthcare Research and Quality (AHRQ), the occurrence of pressure ulcers in patients has risen 63% over the last ten years. Accordingly, attempts to maximize temperature exchange and reduce pressure while a patient is on a mattress have been made over the years.

For example, U.S. Pat. No. 6,874,185 to Phillips et al discloses a foam core cushion mattress assembly having semi-independent foam pillars on the upper surface of the mattress. The mattress may be unitary, or comprise multiple cushioning components, possibly base, body support and foot cushions. The body support cushion is constructed from a flat, rectangular solid, foam element whose upper surface is cut into an array of rectangular solid pillars, preferably by a hot wire cutting method. The array of rectangular solid pillars is grouped into a central array comprising pillars with generally square top surfaces and edge rows of rectangular solid pillars having rectangular top surfaces. The depth of the hot wire cuts into the surface of the body support cushion is preferably approximately one-half the overall thickness of the body support cushion or approximately three fourths of the length of the shortest face of the pillar. A zippered fabric cover removeably envelops the assembled cushioning components. The resultant structure defines a plurality of semi-independently compressible pillars that support a reclining, or supine patient. The pillars may also be cut into the top and bottom surfaces of the cushion for enhanced pressure relieving effects. Methods of manufacture, and treatment and alleviation of decubitus ulcer formation are also presented.

U.S. Pat. No. 6,375,674 to Carson discloses a medical pad having a thermal exchange layer capable of absorbing and/or releasing heat to a patient and an adhesive surface disposed on a skin-contacting side of the thermal exchange layer for adhering the pad to the skin of the patient. The thermal exchange layer may comprise a fluid containing layer for containing a thermal exchange fluid capable of absorbing thermal energy from and/or releasing thermal energy to the patient. The pad may also include a conformable, thermally conductive layer between the adhesive surface and the fluid containing layer and an insulating layer on the non-skin contacting side of the fluid containing layer. In some arrangements, transverse members or dimples on insulating base member are provided to define tortuous fluid passageways in fluid containing layer. A fluid circulating system including a pump connected downstream from a fluid outlet and a fluid reservoir connected upstream from a fluid inlet may be employed to circulate the fluid though the fluid containing layer. The fluid is drawn from a reservoir into the fluid containing layer through the inlet and out of the fluid containing layer through the outlet under negative pressure by the pump. When the pad is adhered by the adhesive surface to the skin of the patient, thermal energy is exchangeable between the patient and the fluid circulated within the fluid containing layer to cool and/or warm the patient.

U.S. Pat. No. 5,653,741 to Grant discloses a flexible pad capable of selectably heating or cooling an animal or human body part. The pad is formed of two planar surfaces having at least two side portions disposed between said planar surfaces that are made of a mesh material for air circulation within the pad. One planar surface is made of thermal conductive material having a plurality of thermoelectric modules bonded to the conductive material. The thermoelectric modules transfer heat to or away from the conductive material. A heat sink is attached to the opposing side of each modules for dissipating heat from the conductive material during the cooling process. A rheostat has a reversing switch for changing polarity of the rheostat to either transfer heat to the thermoelectric modules and to the planar surface, or from the thermoelectric module to the heat sink.

Further, U.S. Pat. No. 5,564,142 to Liu discloses an air mattress having a plurality of symbiotic sacs juxtapositionally transversely secured in a mattress envelope, having a plurality of primary and secondary symbiotic sacs alternatively pulsated in the envelope for continuously changing the pressurized areas of a bed-ridden patient for preventing pressure sores such as bed sore or decubitus ulcer, with each symbiotic sac consisting of an upper pulsating sac portion alternatively inflated and deflated and a lower static sac portion constantly inflated to maintain at least a partial fluid pressure in each symbiotic sac for continuously cushioning the patient even when a power failure is caused or bed transfer is required, and having a plurality of tertiary symbiotic sacs constantly inflated for cushioning a patient head portion, with each symbiotic sac independently secured in the mattress envelope whereby upon breaking of any one sac, only an individual broken sac should be replaced with a new one without abandoning the whole mattress.

However, these patents fail to describe a pressure variable thermal adaptive microclimate surface and thermoelectric cells for a microclimate surface which efficiently reduces the occurrence of pressure ulcers. Further, these patents fail to describe a pressure variable thermal adaptive microclimate surface and thermoelectric cells for a microclimate surface which efficiently exchanges heat and increases comfort.

SUMMARY OF THE INVENTION

A pressure variable thermal adaptive microclimate surface is provided. The microclimate surface may be a pad, pillow, mattress or the like. The microclimate surface is especially suitable for providing optimal heating and/or cooling of a person. The heating or cooling is provided through heating or cooling delivery system located in the sculpted polyurethane foam microclimate surface. The microclimate surface has a plurality of independently moving pillars which is optimal in reducing pressure ulcers on the skin of a person caused by the person spending extended periods of time on a typical surface, such as a hospital mattress. The heating or cooling delivery system may be provided through three possible configurations: I) Fluid (cooled or heated) is circulated through a tubing matrix which is placed within the sculpted foam surface using a connected thermoelectric device. The electrically powered device consists of one or more thermoelectric cells, a power supply, a pump, a heat exchanger, a fan, electronic thermostatic controller, and a control panel with a user interface (temperature readout, power on/off, set temp, it may or may not have a timer function); II) Fluid (cooled or warmed) is circulated through a tubing matrix which is placed within the sculpted foam surface using a radiator device. The electrically powered radiator device may be integrated within the mattress or in a separate tubing connected component. The radiator device consists of a pump, a heat exchanger with or without fan, and a user interface; or III) The third embodiment incorporates a plurality of small thermoelectric cells which are connected by wiring and inserted into chambers cut into the sculpted foam. These thermoelectric cells are placed so that the thermal therapy side (cooling in this instance) come in closer contact to the patient's body presenting the greatest pressure to the surface. A circulating system of fluid (air or water) is used to draw heat away from the warm side of the thermoelectric cells. This system incorporates a heat exchanger, fluid pump or blower, a controller and a user interface. All three systems may also incorporate one or more separate sensors which can be placed to detect the temperature in localized areas to optimize the setting.

An advantage of the present pressure variable thermal conductive adaptive microclimate surface is that the microclimate surface efficiently controls temperature optimizing delivery of heat or cooling to areas of the body which are being subject to the highest pressure.

Yet another advantage of the present microclimate surface is that the present microclimate surface efficiently reduces pressure on the skin of a person through independently moving ergonomically fitting pillars which reduce both pressure (vertical force) and shear friction (horizontal force).

Yet another advantage of the present microclimate surface is that the present microclimate surface can provide a warm or cool surface for an individual.

Still another advantage of the present microclimate surface is that, in an embodiment, the microclimate surface may include one or more thermoelectric cells which electrically control the temperature of the microclimate surface.

Still another advantage of the present microclimate surface is that the present microclimate surface may have an antibacterial agent added to the water (or other liquid), which is used in the heat exchange, to reduce the possible spread of pathogens.

Yet another advantage of the present microclimate surface is that the present microclimate surface is much thinner than a typical microclimate surface/mattress used for patients.

Another advantage of the present microclimate surface is that the present microclimate surface only requires a small, quiet pump to provide the heat exchange or a small, quiet pump and a blower which may circulate ambient air to facilitate heat exchange.

Still another advantage of the present microclimate surface is that the present microclimate surface requires less energy than other heat exchange surfaces in that the present microclimate surface utilizes a smaller pump and/or smaller blower for heat exchange.

Yet an advantage of the present microclimate surface is that the present microclimate surface may be configured as a mattress or an overlay which may have a strap which may allow the device to be secured to a mattress or bed.

Another advantage of the present microclimate surface is that the present microclimate surface is properly electrically grounded therein eliminating injury from possible electrical shock.

Still another advantage of the present microclimate surface is that the present microclimate surface may be cleaned and reused as opposed to other microclimate surfaces which are generally single-use patient surfaces which must be disposed of after the patient leaves the hospital or after approximately one month (whichever occurs first).

And another advantage of the present microclimate surface is that the present microclimate surface provides a sanitary environment for a patient of a hospital.

Yet another advantage of the present microclimate surface is that the present microclimate surface may utilize a liquid cooling device (as opposed to air cooling) which therein eliminates bacteria or other harmful elements from becoming airborne, as is common in other air-cooled microclimate surfaces. The liquid cooling agent of the present microclimate surface may be circulated throughout the device, as opposed being constantly drawn in and exhausted as in other standard cooling microclimate surfaces.

And an advantage of the present microclimate surface is that the present microclimate surface may use a cooling agent such as a liquid for the heat exchange which is approximately twenty-five times more efficient than air used for heat exchange (as is common in other microclimate surfaces).

Yet another advantage of the present microclimate surface is that the present microclimate surface may be zoned such that a user may selectively and independently control the heating or cooling of specific portions of the surface of the device, such as, for example, only cooling the middle of the device to treat the user's back.

Still another advantage of the present microclimate surface is that the present microclimate surface provides pressure variable thermal transfer/cooling.

An advantage of the present pressure variable thermal conductive adaptive microclimate surface is that the microclimate surface efficiently controls temperature by moving a warm and/or cool agent (typically water or air) through a matrix of tubes.

Still another advantage of the present microclimate surface is that the present microclimate surface is light weight.

And another advantage of the present microclimate surface is that the present microclimate surface has channels which prevent the unwanted movement of the heating and cooling tubes.

Still another advantage of the present microclimate surface is that, in an embodiment, the microclimate surface may include a microchip which electrically controls the temperature of the microclimate surface.

Yet another advantage of the present microclimate surface is that the microclimate surface may have a heating or cooling tube which may be removed for repair or replacement.

For a more complete understanding of the above listed features and advantages of the present pressure variable thermal adaptive microclimate surface and thermoelectric cells for a microclimate surface, reference should be made to the detailed description and the drawings. Further, additional features and advantages of the invention are described in, and will be apparent from, the detailed description of the preferred embodiments.

DETAILED DESCRIPTION OF THE PREFERRED EMBODIMENTS

A pressure variable thermal adaptive microclimate surface is provided. The microclimate surface may be a pad, pillow, mattress or the like. The microclimate surface is especially suitable for providing optimal heating and/or cooling of a person. The heating or cooling is provided through a heating or cooling agent passing through a tube matrix which may be located in the sculpted foam microclimate surface. The microclimate surface has a plurality of independently moving pillars which is optimal in reducing pressure ulcers on the skin of a person caused by the person spending extended periods of time on a typical surface, such as a hospital mattress. The heating or cooling is also provided through a plurality of thermoelectric cells connected to metallic wires wherein the metallic wires pass through a matrix located in the sculpted polyurethane foam microclimate surface. The metallic wire has a cool loop portion and a warm loop portion wherein the cool loop portion may be located on the patient side of the mattress and the warm loop portion located within a cooling agent (such as a gas or a liquid) environment wherein the heat is removed by a circulating cooling fluid agent.

Figure 1:
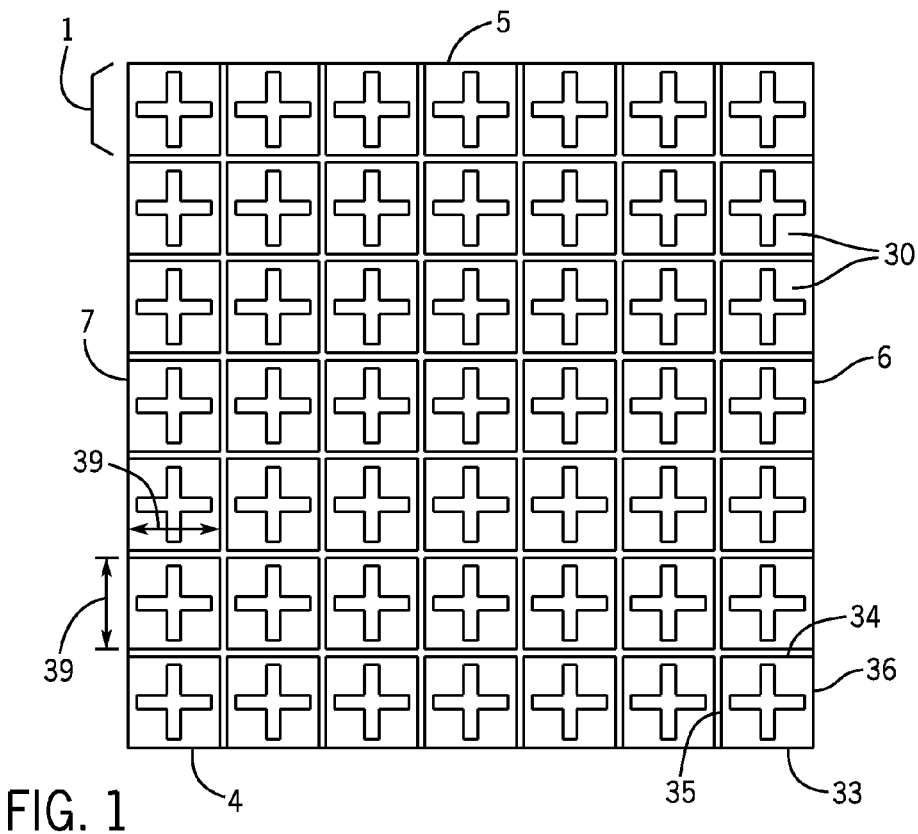
FIG. 1 illustrates a top view of the microclimate surface in an embodiment.
Figure 2:
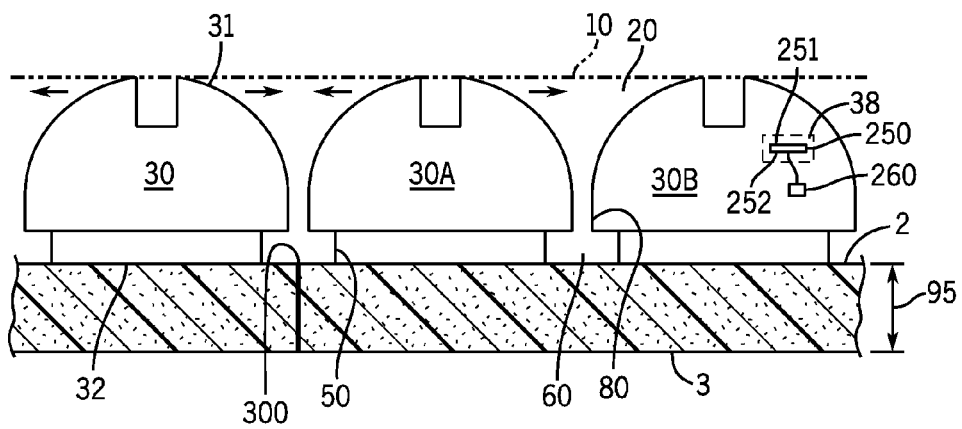
FIG. 2 illustrates a side view of an embodiment of the microclimate surface wherein the heating/cooling tube is not present.

Referring now to FIGS. 1 and 2, a pressure variable thermal conductive adaptive microclimate surface 1 is provided. The microclimate surface 1 may be made largely of, for example, polyurethane memory foam which may be suitable for efficient thermal exchange. The microclimate surface 1 may have a base 95 having a top 2, a bottom 3, a front 4, a back 5, a first side 6 and a second side 7. In an embodiment, a cover 10 may be placed over at least the top 2 (and top 31 of a plurality of pillars 30 as described below) of the microclimate surface 1 so as to keep the microclimate surface 1 clean and functioning properly. When the cover 10 is inserted over the top 2 (and top 31 of the pillars 30) of the microclimate surface 1, an interior space 20 is created between the cover 10 and the microclimate surface 1.

As stated above, the microclimate surface 1 may have a plurality of pillars 30. The plurality of pillars 30 may be elastic (and in an embodiment made of the same material as the base 95) so as to be comfortable and to allow the insertion and removal of a tube 75 (as defined below). Further, in an embodiment, the plurality of pillars 30 may be made as a single unit with the base 95 wherein a solid piece of, for example, polyurethane is cut to form the base 95 and connected pillars 30 of the device 1.

The plurality of pillars 30 may have a top 31 (FIG. 2), a bottom 32, a front 33, a back 34, a first side 35, a second side 36 and, in an embodiment, an interior 38. The front 33, back 34, first side 35 and second side 36 may each have a length 39 (FIG. 1). In an embodiment, the length 39 of the front 33, back 34, first side 35 and second side 36 may all be substantially similar so that each of the plurality of pillars 30 are roughly square in shape (at the bottom 32). The top 31 of the plurality of pillars 30 may be generally domed-shaped. More specifically, the front 33, back 34, first side 35 and second side 36 may all arc inward toward the top/center of the plurality of pillars 30. As a result, the pressure exerted on a body by the pillars 30 is reduced and the device 1 is more comfortable.

Figure 4:
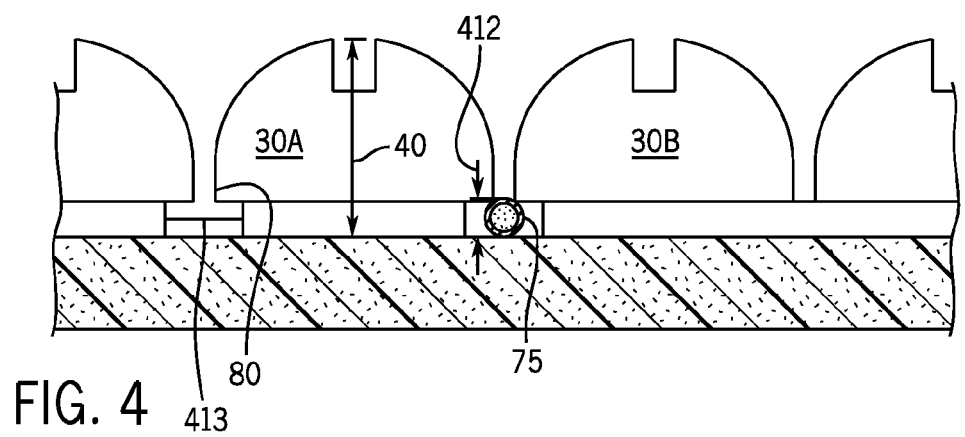
FIG. 4 illustrates a side view of an embodiment of the microclimate surface wherein the heating/cooling tube is already inserted between two of the plurality of pillars.

The front 33, back 34, first side 35 and second side 36 of the plurality of pillars 30 may further have a height 40 (FIG. 4). The height 40 of the front 33, back 34, first side 35 and second side 36 may be substantially similar and may be substantially similar to the length 39 of the plurality of pillars 30 such that each of the plurality of pillars 30 is generally in the shape of a cube (with the exception of the arced top 31 in an embodiment as described above). Because the plurality of pillars 30 is only secured (at the bottom 32 of the pillars 30) to the top 2 of the base 95, the top 31 and sides of the plurality of pillars 30 may move largely independently from one another while the bottom 32 of the pillars 30 remain generally stationary. More specifically, the bottom 32 of the plurality of pillars 30 is secured to the top 2 of the microclimate surface 1. The bottom 32 of the pillars 30 is secured directly to the top 2 of the microclimate surface 1 wherein the top 31, front 33, back 34, first side 35 and second side 36 are unsecured and may move with respect to the microclimate surface 1.

The front 33, back 34, first side 35 and second side 36 of the plurality of pillars 30 may have an indentation 50. The indentation 50 may be generally rectangular in shape (or in an embodiment not shown semi-circular) and may have a length which extends the entire length 39 of the front 33, back 34, first side 35 and second side 36 of the pillars 30 (surrounding each of the plurality of pillars 30). In an embodiment, the indentation 50 is located substantially near the bottom 32 of each of the plurality of pillars 30 so that a tube 75 (as described below) remains secure and protected by the top 31 of the pillars 30 when a person is lying on the device 1.

In an embodiment, a first pillar 30A is located directly next to a second pillar 30B. As a result of at least two of the plurality of pillars 30A, 30B being located directly next to each other, the indentation 50 of the first pillar 30A aligns with the indentation 50 of the second pillar 30B such that the two indentations 50 come together to form a generally rectangular passageway 60 between the two pillars 30. The generally rectangular passageway 60 may have a width 413 which is greater than a width 412 of the tube 75 such that the tube 75 fits snugly within the generally rectangular passageway 60 (as further described below).

The first pillar 30A may be secured to the second pillar 30B just below the indentation 50. The generally rectangular passageway 60 formed from two of the indentations 50 of the plurality of pillars 30 may have a single slit 80 (FIG. 4) facing upward (away from the top 2 of the base 95 of the device 1). More specifically, the single slit 80 may be created from two of the plurality of pillars 30 being aligned directly adjacent to each other.

Locating the indentation 50 near the bottom 32 of the plurality of pillars 30 greatly reduces the stress on the tubes 75 while the device 1 is in use. More specifically, as the weight of the person presses down upon the top 31 of the plurality of pillars 30, the tubes 75 remain largely unaffected as they are located near the protected bottom 32 of the pillars 30.

Figure 3:
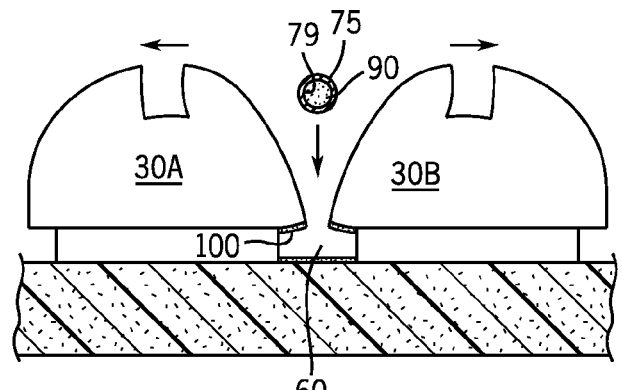
FIG. 3 illustrates a side view of an embodiment of the microclimate surface wherein the heating/cooling tube is in the process of being inserted into the generally cylindrical passageway of the plurality of pillars.

As stated above, the tube(s) 75 may be secured within the generally rectangular passageway 60 of the device 1. The tube 75 may have a first end 76 (FIG. 5), a second end 77, a length and a generally hollow interior 79 (FIG. 3). The tube 75 may be flexible so as to allow the tube 75 to bend at various angles (generally ninety degrees) through the generally rectangular passageways 60 of the plurality of pillars 30. The first end 76 may be an inlet wherein a warming or cooling agent 90 (such as hot or cold gas or a hot or cold liquid) may be pumped through the tube 75. The second end 77 may be a return end wherein the warming or cooling agent 90 is reheated or re-cooled and then returned through the system. As a result of pumping a warming or cooling agent 90 through the tube 75, the temperature of the device 1 (and therein the person located on the device 1) may be easily controlled.

Figure 5:
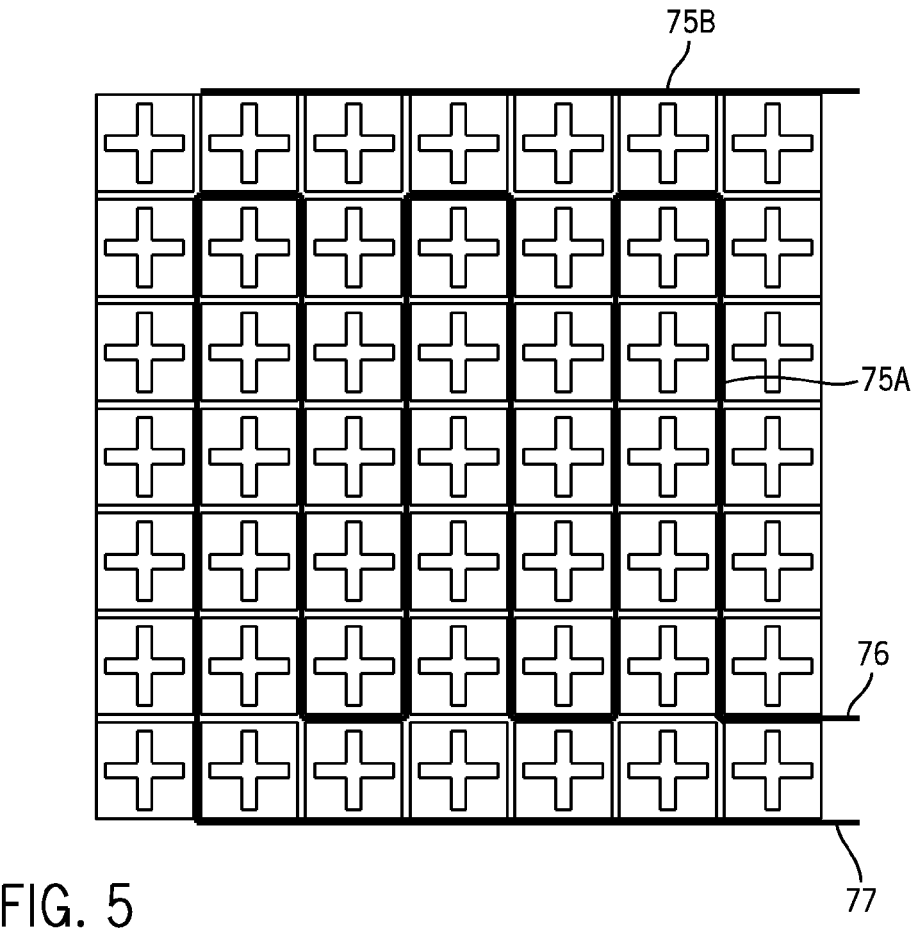
FIG. 5 illustrates a top view of an embodiment of the microclimate surface wherein the heating/cooling tube is visible.

In an embodiment, a manufacturer or user may elect which of the generally rectangular passageways 60 to insert the tube 75 through so that temperature may be controlled properly. For example, a manufacturer may elect to place the tube(s) 75 just under the area of the device 1 wherein most of the weight of the person would be concentrated. In an embodiment, a manufacturer may elect to have two or more separate tubes 75 such that one tube 75A circulars a warming agent and a second tube 75B circulates a cooling agent 90 (FIG. 5).

Referring now to FIG. 3, to insert the tube 75 into the generally rectangular passageway 60, the manufacturer or user slightly pulls two of the plurality of pillars 30 away from each other; therein increasing the size of the slit 80. As the slit 80 size is increased enough to accept the tube 75, the tube 75 may be placed into the generally rectangular passageway 60 and the pillars 30 therein allowed to relax back to their normal state. Preferably, the tubes 75 remain secured within the generally rectangular passageways 60 by, for example, only friction. As a result, a user may pull two of the pillars 30 away from each other to repair, replace or entirely remove the tube 75. It should be noted that in an embodiment, an adhesive 100 (such as sprayed-on glue) may be placed in the generally rectangular passageway to better secure the tube 75 through the pillars 30. Of course, the addition of the adhesive 100 reduces the ease of later removing the tube 75 from the device 1.

In an embodiment, the interior 38 of the plurality of pillars 30 may have an electronic heating and cooling chip 250 (thermoelectric chip shown in FIG. 2) which is in electrical communication with a power source 260. The electronic heating and cooling chip 250 may have a first side 251 and a second side 252 wherein the first side 251 may be electrically powered to produce a cooling effect while the second side 252 produces heat. In an embodiment, the first side 251 faces upward, toward the top 31 of the plurality of pillars 30. As a result, the top 31 of numerous of the plurality of pillars 30 may produce a cooling effect which is transferred to an individual lying on the microclimate surface 1.

As stated above, the top 31 of the plurality of pillars 30 is domed-shaped. Providing a plurality of pillars 30 which has domed-shaped tops 31, along with the protective generally rectangular passageway 60 between the plurality of pillars 30 allows the exterior surface of the tube 75 carrying the warming or cooling agent 90 to remain protected and generally cylindrical in shape (largely unchanged even under the weight of the person). More specifically, when weight (pressure) is applied to existing warming or cooling mattresses by a person, the weight of the person is transferred to the exterior surface of the warming or cooling tube causing the tube to adopt an elliptical shape rather than the desired cylindrical shape maintained by the present device. When the tube of other devices is compressed into the elliptical shape, the warming or cooling agent does not flow properly and the device is not as effective at transferring the warming or cooling agent (air or water) throughout the mattress. Because the tube(s) 75 of the present device 1 maintains a generally cylindrical exterior surface as a result of the domed-shape tops 31 and the protective generally rectangular passageway 60, the warming or cooling agent 90 of the present device 1 may be properly transferred through the tube 75 and the desired temperature may be maintained on the skin of the person.

In addition to the plurality of pillars 30 having domed-shaped tops 31 and the generally rectangular passageway 60 both protecting tube 75, the air spaces/bubbles in the plurality of pillars 30 may be reduced upon compression. Therefore, the insulating capability (r value) of the present device 1 is reduced and the thermal transfer rate (conduction) from the circulated warming or cooling agent 90 through the compressed plurality of pillars 30 to the person's skin is highest where the plurality of pillars 30 is most compressed. This high pressure area is the location where pressure ulcers would normally form and where the warming or cooling agent 90 can provide the greatest benefit. This process is effective on both memory foam (closed cells) and conventional foam (open cells) microclimate surfaces. More specifically, the process reduces the skin surface temperature at high pressure sites. Normally, high skin surface temperature is aggravated by the lack of airflow between the patient and the mattress surface, which is typically covered in a moisture impermeable fabric to reduce the risk of infection. The body (endocrine system) senses high temperatures at the site and increases sweat production in an effort to create evaporative cooling. Without airflow there is no evaporation and the skin gets waterlogged (macerated). Macerated skin is weakened and can be damaged more easily leading to infection and pressure ulcers. These problems are reduced or eliminated by the present device 1.

The primary therapeutic benefit of the device 1 is that the device 1 helps keep skin temperatures in a normal range. This means that in most all cases, the device 1 provides cooling rather than heating due to the construction of most healthcare surfaces. Most healthcare surfaces, are made using a fluid proof top surface to facilitate cleaning and help reduce the spread of infections. The fluid proof surfaces do not allow heat which is normally generated by the human body to dissipate. The heat builds up and causes two problems: (1) The body's endocrine system senses high temperatures and then triggers the localized sweat glands to secrete perspiration in an effort to provide evaporative cooling. Since there is no air movement between a patient and the mattress surface the moisture is trapped, there is no cooling and even more sweat accumulates and causes the skin to become macerated and much more subject to damage due to pressure and friction. Affected patients can eventually become dehydrated and exhibit other symptoms that can be hard to diagnose and treat. (2) Higher than normal temperatures alone also increase the biological demand of the skin in the affected areas. This causes the skin cells to operate at a reduced level of performance leading to higher susceptibility to damage and reduced healing rates.

One published study showed that cellular biological demand (the energy needed to properly function) was increased 10% for every degree c above normal. Another study noted that a 5 degree c reduction was comparable to the therapeutic benefit of the highest technology mattresses versus a standard mattress.

In an embodiment, the device 1 may be cooling only. The overall construction and design of cooling versus heating and cooling units may be identical. The heat/cool designs just add electrical components to change the polarity of the DC power (from positive to negative) to the thermoelectric modules and this changes them from cold to hot.

Figure 6:
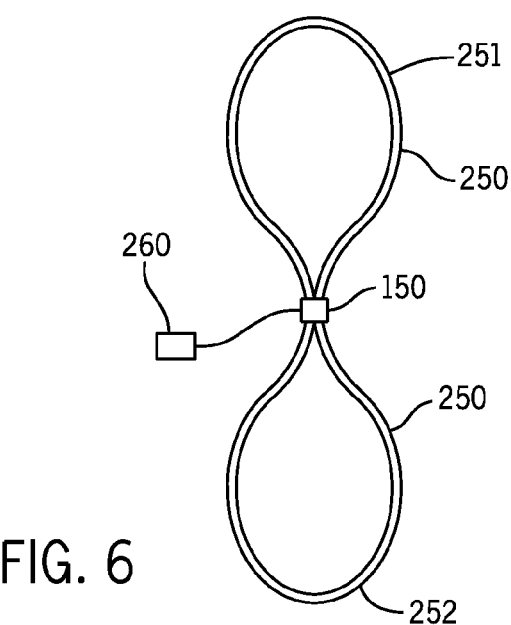
FIG. 6 illustrates a front view of an embodiment wherein a thermoelectric cell connected to a metallic strip is utilized for heating or cooling the mattress.

Referring now to FIG. 6, in an embodiment, the microclimate surface 1 may further have at least one thermoelectric cell (also referred to as a cooling chip) 150 connected to a power source 260. It should be noted that the device 1 preferably has numerous thermoelectric cells 150 and that the term thermoelectric cell 150 in the present application may be read as plural. The thermoelectric cell 150 may be electrically and mechanically secured to a metallic strip (or wire) 250. In an embodiment, the metallic strip 250 may take the form of a braided metallic strip. Alternatively, in an embodiment, the metallic strip 250 may be generally flat and may have a first loop portion 251 and a second loop portion 252. The thermoelectric cell 150 may power and control the metallic strip 250. When energy is added to the thermoelectric cell 150, the thermoelectric cell 150 may control the temperature of the first loop portion 251 and second loop portion 252. In an embodiment, the thermoelectric cell 150 may make the first loop portion 251 generally cool and may make the second loop portion 252 generally warm. The energy source may be, for example, DC or 110-250 VAC which is then converted to 12-24 Volts DC, 3-6 Amps to power the thermoelectric cells 150 and/or ancillary pump and blowers.

More specifically, the thermoelectric cell 150 consists of a number of p- and n-type pairs (couples) connected electrically in series and sandwiched between two ceramic plates. When connected to a, for example, DC power source, current causes heat to move from one side of the thermoelectric cell to the other. This creates a hot side and a cold side on the thermoelectric cell. As a result, the thermoelectric cell 150 may allow the first loop portion 251 to remain at approximately sixty-five degrees F. whereas the second loop portion 252 remains at approximately eighty-five degrees F.

In an embodiment, the first loop portion 251 is located on the top 2 of the base 95 (FIG. 7) and the second loop portion 252 is located beneath the top 2 of the base 95. The thermoelectric cell 150 may be located between the first loop portion 251 and the second loop portion 252 so that when the thermoelectric cell 150 is activated, the first loop portion 251 cools down and the second loop portion 252 warms up. An opening 300 (FIG. 7) may be present extending from the top 2 of the base 95 through toward the bottom 3 of the base 95. The opening 300 may create a channel allowing the thermoelectric cell 150 to be located both on the top 2 and within the interior (or in an embodiment the bottom 3) of the base 95 wherein the first loop portion 251 extends to and remains substantially on the top 2 of the base 95 and the second loop portion 252 extends to and remains substantially within the interior of the base 95. As a result, the top 2 of the base 95 (the side which a patient rests on) remains cools and the heat is transferred to the interior of the base 95 and away from the patient. Further, in an embodiment, the first loop portion 251 rests around the pillars 30 in a substantially parallel position with respect to the base 95 whereas the second loop portion 252 rest within the interior of the base 95 in a substantially perpendicular position with respect to the base 95. Further, in an embodiment, the first loop portion 251 is located in the generally rectangular passageways 60 surrounding a single pillar 30.

In an embodiment, the base 95 has a plurality of openings 300 such that numerous thermoelectric cells 150, each having a first loop portion 251 and second loop portion 252) are used throughout the base 95. More specifically, the device 1 may have, for example, approximately one thermoelectric cell 150 for every one and a half pillars 30 such that one thermoelectric cell 150 is located between a quadrant of four pillars 30. As a result, the first loop portion 251 covers a substantial portion of the entire top 2 of the base 95 therein insuring that the patient remains cool regardless of where on the surface the patient is located.

Figure 7:
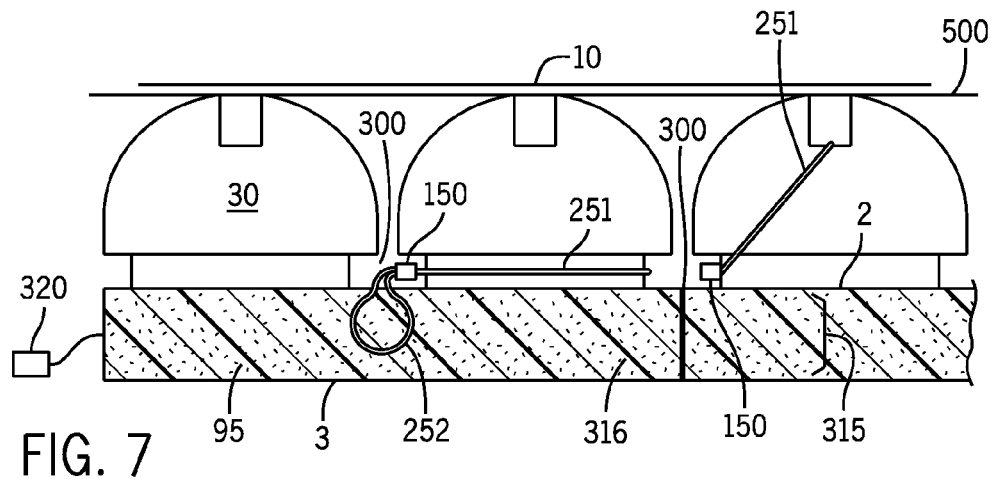
FIG. 7 illustrates a side view of an embodiment wherein the thermoelectric cell is inserted around a pillar on one end and within the mattress at the other end.
Figure 8:
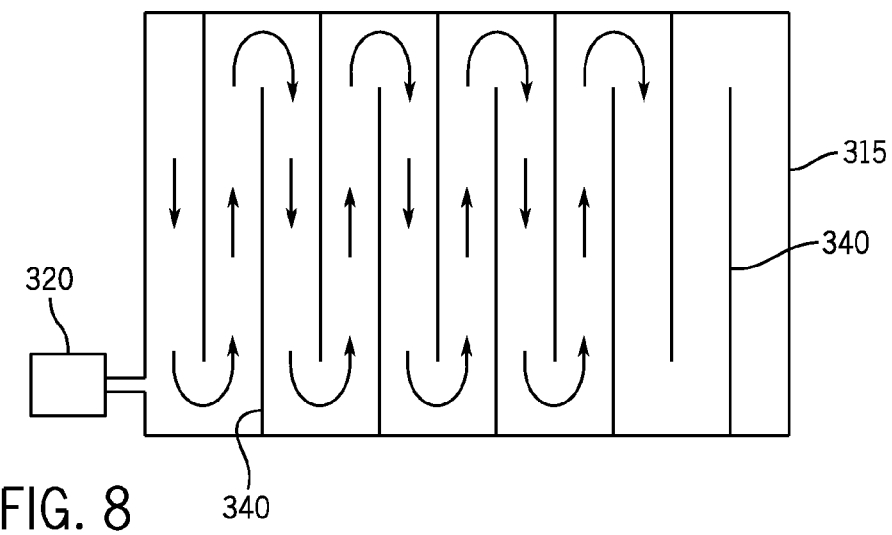
FIG. 8 illustrates a top view of the flow of a fluid through the mattress.

In an embodiment, the second loop portion 252 may be substantially located in a cooling agent containment 315 (FIG. 7). More specifically, in this embodiment, the base portion 95 may be hollow and may contain a cooling agent 316. The cooling agent containment 315 may be a generally rectangular durable bag or other securing mechanism wherein the cooling agent 316 is present. Preferably the cooling agent 316 is liquid water; however, the cooling agent 316 may be any suitable agent including other liquids, a gas or a liquid combination. The cooling agent 316 may allow the heat from the second loop portion 252 to escape from the metallic strip 250 into the cooling agent 316. As the cooling agent 316 is circulated throughout the cooling agent containment 315 by means of a pump 320, the heat may be removed from the system so as to allow the top 2 of the base 95 (and therefore the patient) to remain cool. Further, an antibacterial agent may be added to the cooling agent 316 to prevent the spread of pathogens. A waterproof seal may be located within or near the plurality of openings 300 such that cooling agent 316 located within the cooling agent containment 315 may not escape the cooling agent containment 315. An embodiment, the cooling agent containment 315 may have partial separating walls 340 (FIG. 8) which may force the cooling agent 316 to move in a predetermined direction (for example, in a spiral manner or in a zigzag pattern).

In an alternative embodiment, the device 1 may utilize a flexible tubing system to carry the cooling agent 316 as opposed to the above-mentioned cooling agent 316 flowing through a cooling agent containment 315. In this embodiment, the flexible tubing may reduce restriction of the assembly from the flexing and conforming to the body of the user thus aiding pressure redistribution. In this embodiment, the flexible tubing may be located below the bottom 3 of the base 95 of the microclimate surface 1 and may be placed in proximity to the warm second loop portion 252 (which may be braided) so as to cool the thermoelectric cells 150 rather than carrying the cooling agent 316 close to the top surface 2 of the base 95. With respect to the pressure redistribution, by allowing the base 95 to flex freely, the present device may reduce a "hammocking" effect which often concentrates vertical forces rather than allowing them to be dissipated.

As stated above, the microclimate surface 1 may have a plurality of pillars 30. The plurality of pillars 30 may be elastic (and made of the same material as the base 95) so as to be comfortable and to allow the insertion and removal of the first loop portion 251. Further, the plurality of pillars 30 may be made as a single unit with the base 95 wherein a solid piece of, for example, polyurethane is cut to form the base 95 and connected pillars 30 of the device 1.

As stated above, the top 31 of the plurality of pillars 30 is domed-shaped. Providing a plurality of pillars 30 which has domed-shaped tops 31, along with the protective generally cylindrical passageway 60 between the plurality of pillars 30 allows the first loop portion 251 (the cool portion) of the metallic strip 250 to not only remain protected by the pillars 30, but the protective generally cylindrical passageways 60 and pillars 30 also increases the comfort for the user by providing a buffer between the user and the metallic strip 250. More specifically, the device increases patient comfort when weight (pressure) is applied to plurality of pillars 30 as opposed to being applied to the first loop portion 251 of the metallic strip 250.

Figure 9:
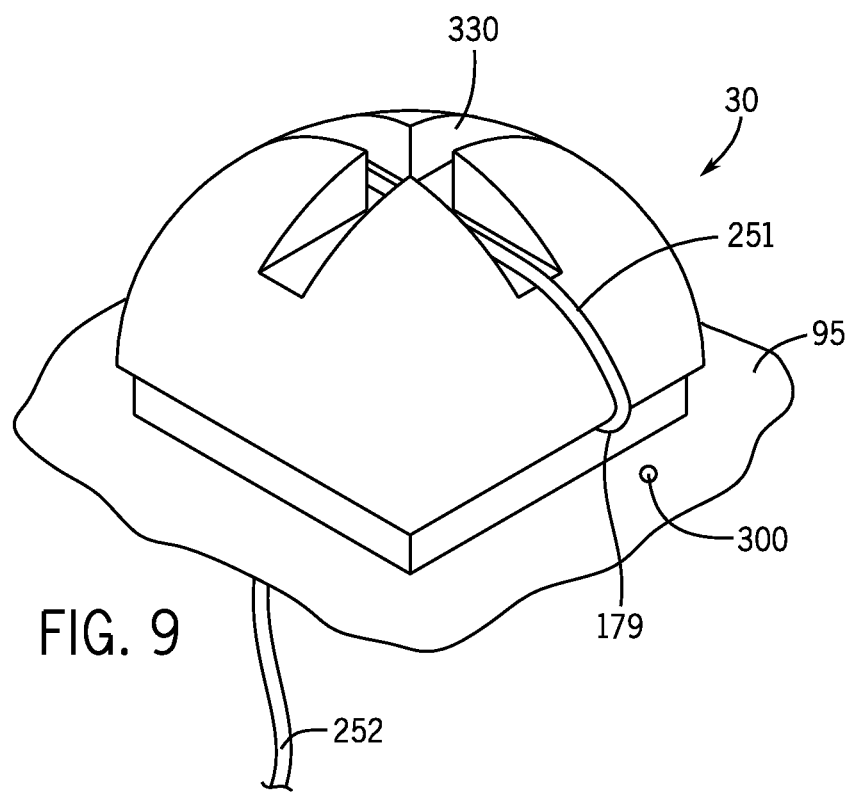
FIG. 9 illustrates a perspective view of the top of a pillar in an embodiment wherein the thermoelectric cell is secured through a passageway on the top of the pillar.

Referring now to FIG. 9, in an embodiment, the domed-shaped tops 31 of the plurality of pillars 30 may have a generally cross-shaped channel 330 for which the first loop portion 251 of the metallic strip 250 may pass through. The cross-shaped channel 330 may allow the first loop portion 251 to reach over the top 31 of the plurality of pillars 30 and remain secured to the top 31 of the pillars 30 without the first loop portion 251 accidently sliding off the top 31 of the pillars 30.

The insulating capability (r value) of the present device 1 is reduced and the thermal transfer rate (conduction) from the first loop portion 251 to the person's skin is highest where the plurality of pillars 30 is most compressed. This process is effective on both memory foam (closed cells) and conventional foam (open cells) microclimate surfaces. More specifically, the process reduces the skin surface temperature at high pressure sites. Normally, high skin surface temperature is aggravated by the lack of airflow between the patient and the mattress surface, which is typically covered in a moisture impermeable fabric to reduce the risk of infection. The body (endocrine system) senses high temperatures at the site and increases sweat production in an effort to create evaporative cooling. Without airflow there is no evaporation and the skin gets waterlogged (macerated). Macerated skin is weakened and can be damaged more easily leading to infection and pressure ulcers. These problems are reduced or eliminated by the present device 1.

In an embodiment, the device 1 may have a generally flat conductive layer 500 (FIG. 7). The generally flat flexible conductive layer 500 may be placed over the top 31 of the plurality of pillars 30 (and beneath the cover 10). The generally flat conductive layer 500 may be grounded such that any electrical charge from the thermoelectric cells 150 which may improperly otherwise contact the patient would be grounded rendering the device 1 safe and harmless.

In an embodiment, the top 2 of the microclimate surface 1 may be zoned such that specific predetermined areas may be selectively heated, cooled or not activated. More specifically, a user may, for example, independently and selectively control the thermoelectric cells 150 around, for example, only the middle of the user's back wherein the remaining thermoelectric cells 150 located on the top 2 of the microclimate surface 1 are not activated or are activated at different temperatures. Further, in this embodiment, a computer monitor may display different areas of the microclimate surface 1 or the computer monitor may illustrate representations of different areas of a user's body to allow the user to independently select different temperatures for different areas.

In an embodiment, the microclimate surface 1 of the present device may be used in conjunction with other mattresses wherein the other mattresses may have alternating pressurized areas. As a result, one may control not only the temperature, but also the pressure exerted on him/herself.

Figure 10:
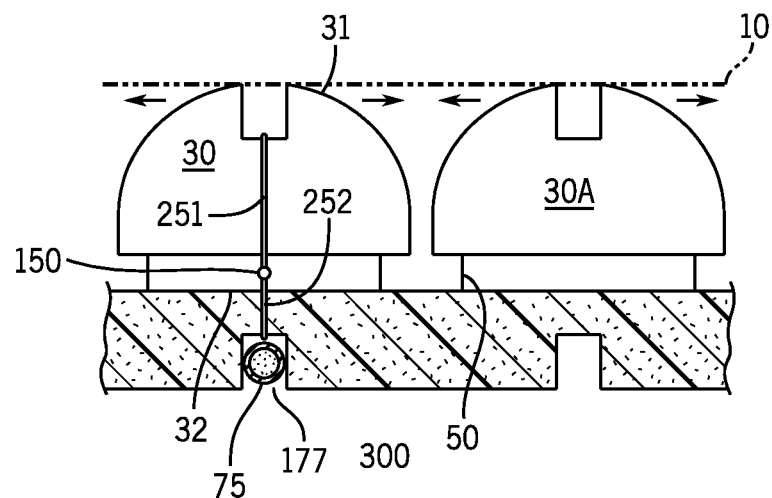
FIG. 10 illustrates an embodiment wherein the bottom of the base portion has an opening and utilizes both the tube circulating a liquid or gas and the thermoelectric cell.

Referring now to FIG. 10, in an embodiment, an additional opening 177 may be located on the bottom 3 of the base 95. The opening 177 at the bottom 3 of the base 95 is preferably located directly below the center of each of the plurality of pillars 30. The opening 177 is preferably slightly greater in width than the width 412 of the tube 75 such that the tube 75 may snugly fit within the opening 177 at the bottom 3 of the base 75. In this alternative embodiment, the device 1 may utilize not only the tube 75 circulating the warming or cooling agent 90 but also the thermoelectric cell 150 having the first loop 251 and the second loop 252. In this embodiment, the user may wish, for example, the first loop 251 to provide a cool surface for the top of the device 1. When the first loop 251 is cool, the second loop 252 becomes conversely warm. The heat from the second loop 252 is then transferred to a cooling agent 90 located in the tube 75 within the second opening 177 directly below the second loop 252.

Figure 11:
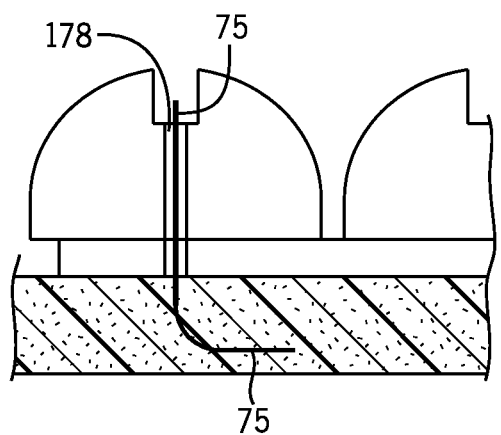
FIG. 11 illustrates an embodiment wherein the tube utilizing the liquid or gas extends through the center of one of the plurality of pillars.

Referring now to FIG. 11, in an alternative embodiment, an opening 178 may be located within the center of the plurality of pillars 30. In this embodiment, the tube 75 (or the first loop 251 of the thermoelectric cell 150) may extend directly through the center of at least one of the plurality of pillars 30. In yet another embodiment, an opening 179 (FIG. 9) may be located on the side of one of the plurality of pillars 30 wherein the tube 75 (or first loop 251 of the thermoelectric cell 150) may pass through the opening 179 in the side of the plurality of pillars 30. In the embodiment wherein the thermoelectric cell 150 is utilized (such as in FIG. 9), the second loop 252 extends down below the plurality of pillars 30.

Finally, in an embodiment, the top 2 surface of the base 95 of the microclimate surface 1 maybe cooled solely by the heat exchange from a cooling agent 316 through tubing placed on the top surface 2 of the base 95 wherein the cooling agent 316 is pumped and circulated through the tubing by means of a heat exchanger and blower.

Although embodiments of the invention are shown and described therein, it should be understood that various changes and modifications to the presently preferred embodiments will be apparent to those skilled in the art. Such changes and modifications may be made without departing from the spirit and scope of the invention and without diminishing its attendant advantages.

I claim:

1. A thermal microclimate surface comprising:
   a base portion wherein the base portion has a top, a bottom, a front, a back, a first side and a second side;
   a plurality of pillars wherein the plurality of pillars have a top, a bottom, a front, a back, a first side and a second side;
   wherein the bottom of the plurality of pillars is permanently secured to the top of the base portion;
   a space forming a channel located between two of the plurality of pillars wherein the first side of one pillar, the second side of an adjacent pillar and the top of the base portion form the space forming a channel;
   wherein each of the plurality of pillars shift independently;
   a tube having a first end, a second end and a diameter wherein the tube is inserted within the space between two of the plurality of pillars or directly through an opening in the center of the plurality of pillars and wherein the tube is secured by the space between the plurality of pillars or the opening in the center of the plurality of pillars;
   wherein a heating or cooling gas or liquid is inserted within the tube and wherein the heating or cooling gas or liquid is used to heat or cool a part of a body of a person;
   an adhesive added to the tube wherein the adhesive secures the tube within the desired spaces between the plurality of pillar.

2. The thermal microclimate surface of claim 1 further comprising:
   a first perimeter formed from the first side, the second side, the front and the back of the plurality of pillars; and
   a second perimeter formed from the first side, the second side, the front and the back of the plurality of pillars wherein the first perimeter is greater than the second perimeter and wherein the portion of the first side, the second side, the front and the back of the plurality of pillars which forms the second perimeter directly contacts the top of the base portion and wherein the first perimeter is elevated above the second perimeter.

3. The thermal microclimate surface of claim 2 wherein the first loop portion of the metallic wire is secured completely around the second perimeter of the plurality of pillars.

4. The thermal microclimate surface of claim 1 further comprising:
   a first channel located on the top of each of the plurality of pillars and a second channel located on the top of each of the plurality of pillars wherein the first channel and the second channel are perpendicular to each other and wherein the first channel and the second channel allow the tube or a wire to be secured over the top of each of the plurality of pillars and prevent the tube or wire from falling off the top of the plurality of pillars.

5. The thermal microclimate surface of claim 1 further comprising:
   a heating or cooling microchip located within an interior of each of the plurality of pillars wherein the heating or cooling microchip heats or cools the plurality of pillars.

6. The thermal microclimate surface of claim 1 wherein the top of the plurality of pillars is domed-shaped.

7. The thermal microclimate surface of claim 1 further comprising:
   a first perimeter formed from the first side, the second side, the front and the back of the plurality of pillars; and
   a second perimeter formed from the first side, the second side, the front and the back of the plurality of pillars wherein the first perimeter is greater than the second perimeter and wherein the portion of the first side, the second side, the front and the back of the plurality of pillars which forms the second perimeter directly contacts the top of the base portion and wherein the first perimeter is elevated above the second perimeter.

8. The thermal microclimate surface of claim 1 wherein the thermal microclimate surface is secured beneath a cover and wherein the tube is selectively secured between the plurality of pillars directly under areas of the body needing to be heated or cooled.

9. A thermal microclimate surface comprising:
   a base portion wherein the base portion has a top, a bottom, a front, a back, a first side and a second side;
   a plurality of pillars wherein the plurality of pillars have a top, a bottom, a front, a back, a first side and a second side;
   wherein the bottom of the plurality of pillars is permanently secured to the top of the base portion;
   a space forming a channel located between two of the plurality of pillars wherein the first side of one pillar, the second side of an adjacent pillar and the top of the base portion form the space forming a channel;
   wherein each of the plurality of pillars shift independently;
   a thermoelectric cell connected to a metallic wire wherein the metallic wire has a first loop portion and a second loop portion and wherein the thermoelectric cell is located between the first loop portion and the second loop portion;
   a power source connected to the thermoelectric cell wherein the power source provides power to the thermoelectric cell; and
   wherein the thermoelectric cell is located within the space between two of the plurality of pillars and wherein the thermoelectric cell heats or cools at least one of the first loop portion or the second loop portion of the metallic wire.

10. The thermal microclimate surface of claim 9 wherein the second loop portion of the metallic wire is secured within an interior of the base portion of the thermal microclimate surface.

11. The thermal microclimate surface of claim 9 wherein the second loop portion of the metallic wire completely passes through an opening in the base portion and wherein the base portion is hollow and wherein the second loop portion of the metallic wire partially is located within the hollow base portion and wherein heat or cold generated by the second loop portion of the metallic wire is passed from the second loop portion into a gas or liquid located within the hollow base portion.

12. The thermal microclimate surface of claim 11 further comprising:
   a partial separating wall located within the hollow interior of the base portion wherein the partial separating wall directs the flow of the gas or liquid located in the hollow interior of the base portion.

13. The thermal microclimate surface of claim 9 wherein the top of the plurality of pillars is domed-shaped.

14. The thermal microclimate surface of claim 9 wherein the first loop portion of the metallic wire completely surrounds a base of one of the plurality of pillars.

15. The thermal microclimate surface of claim 9 further comprising:
   a generally flat flexible conductive metallic layer located over the top of the plurality of pillars wherein the generally flat flexible conductive metallic layer grounds any electrical charge from the thermoelectric cell.

16. The thermal microclimate surface of claim 9 further comprising:
   a first channel located on the top of each of the plurality of pillars and a second channel located on the top of each of the plurality of pillars wherein the first channel and the second channel are perpendicular to each other and wherein the first channel and the second channel allow a tube or wire to be secured over the top of each of the plurality of pillars and prevents the tube or wire from falling off the top of the plurality of pillars; and
   wherein the first loop portion of the metallic wire is secured within the first channel or the second channel located on the top of the plurality of pillars.

17. The thermal microclimate surface of claim 9 wherein the first loop portion of the metallic wire and the second loop portion of the metallic wire have different temperatures.

18. A thermal microclimate surface comprising:
   a base portion wherein the base portion has a top, a bottom, a front, a back, a first side and a second side;
   a plurality of pillars wherein the plurality of pillars have a top, a bottom, a front, a back, a first side and a second side;
   wherein the bottom of the plurality of pillars is permanently secured to the top of the base portion;
   a space forming a channel located between two of the plurality of pillars wherein the first side of one pillar, the second side of an adjacent pillar and the top of the base portion form the space forming a channel;
   wherein each of the plurality of pillars shift independently;
   a thermoelectric cell connected to a metallic wire wherein the metallic wire has a first loop portion and a second loop portion and wherein the thermoelectric cell is located between the first loop portion and the second loop portion;
   a power source connected to the thermoelectric cell wherein the power source provides power to the thermoelectric cell;
   wherein the thermoelectric cell is located within the space between two of the plurality of pillars and wherein the thermoelectric cell heats or cools at least one of the first loop portion or the second loop portion of the metallic wire; and
   a tube having a first end, a second end and a diameter wherein the tube circulates a heated or cooled gas or liquid and wherein heat or cold generated by the second loop portion of the thermoelectric cell is transferred to the heated or cooled gas or liquid located within the tube.

19. The thermal microclimate surface of claim 18 further comprising:
   an opening located in the base and below each of the plurality of pillars wherein the opening received the tube.

* * * * *